United States Patent

Bartmann et al.

[11] 4,312,882
[45] Jan. 26, 1982

[54] THIENYOXY AND FURYL CONTAINING ANALOGS OF PROSTACYCLIN AND THEIR USE AS MEDICAMENTS

[75] Inventors: Wilhelm Bartmann, Bad Soden am Taunus; Elmar Konz, Kelkheim; Ulrich Lerch, Hofheim am Taunus; Bernward Schölkens, Kelkheim, all of Fed. Rep. of Germany

[73] Assignee: Hoechst Aktiengesellschaft, Frankfurt am Main, Fed. Rep. of Germany

[21] Appl. No.: 114,684

[22] Filed: Jan. 23, 1980

[30] Foreign Application Priority Data

Jan. 25, 1979 [DE] Fed. Rep. of Germany ....... 2902809

[51] Int. Cl.³ ................ C07D 307/935; C07D 303/32; A61K 31/557
[52] U.S. Cl. .................................. 424/275; 424/285; 542/426; 542/430
[58] Field of Search ................... 269/346.22; 542/426, 542/429, 430; 424/275, 285

[56] References Cited

U.S. PATENT DOCUMENTS

| | | | |
|---|---|---|---|
| 4,158,667 | 6/1979 | Axen | 260/346.22 |
| 4,178,367 | 12/1979 | Hayashi et al. | 260/346.22 |
| 4,219,479 | 8/1980 | Vorbrüggen et al. | 269/346.22 |

FOREIGN PATENT DOCUMENTS 2819447 11/1978 Fed. Rep. of Germany .

Primary Examiner—John M. Ford
Assistant Examiner—Bernard Dentz
Attorney, Agent, or Firm—Curtis, Morris & Safford

[57] ABSTRACT

What is disclosed are prostacyclin analogs of the general formula I

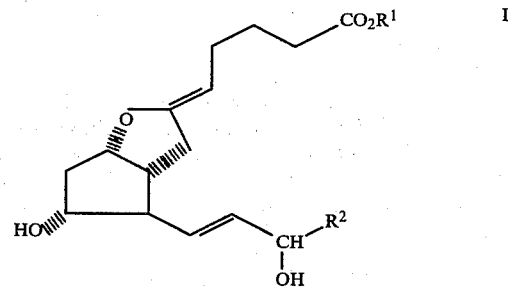

which have a more specific action and/or a longer action than the naturally occurring prostacyclin $PGI_2$, as well as intermediate products for their preparation and a process for their preparation. The compounds of formula I are distinguished by inhibitory action on thrombocyte aggregation and by relaxation of the vascular walls, in particular of the coronary arteries. They can thus be used as medicaments.

5 Claims, No Drawings

THIENYOXY AND FURYL CONTAINING ANALOGS OF PROSTACYCLIN AND THEIR USE AS MEDICAMENTS

Prostacyclin or $PGI_2$, a recently isolated naturally occurring substance of the prostaglandin family, is distinguished by very pronounced inhibitory properties with regard to thrombocyte aggregation (The Lancet 1977, 18). In addition, $PGI_2$ is able to relax some blood vessels, for example coronary arteries (Prostaglandins 13, 3, 1977), so that it could find use in the therapy and prophylaxis of thromboses and infarctions.

The present invention relates to new analogs of the general formula I

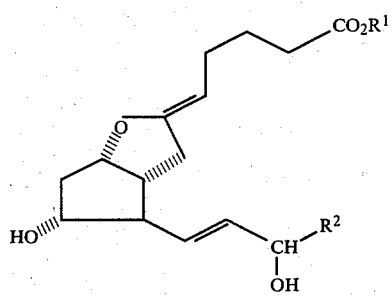

which have a more specific action and/or a longer period of action than $PGI_2$ and in which $R^1$ denotes hydrogen, a straight-chain or branched alkyl radical with up to six carbon atoms, a straight-chain or branched unsaturated aliphatic hydrocarbon radical with three to six carbon atoms, a cycloaliphatic hydrocarbon radical with three to seven carbon atoms, an araliphatic hydrocarbon radical with seven to nine carbon atoms or a physiologically acceptable metal ion or $NH_4$ ion, or ammonium ion which is derived from a primary, secondary or tertiary amine, or a tetraalkylammonium ion and $R^2$ denotes a cycloalkyl radial with 3 to 7 carbon atoms or a straight-chain or branched alkyl radical with up to 8 carbon atoms, which can in turn be substituted by (a) halogen, or an α- or β-thienyl radical or an α- or β-furyl radical, which can in turn be mono-, di- or tri-substituted in the nucleus by halogen, trifluoromethyl and/or alkyl or alkoxy with in each case 1-6 C atoms, or (b) an oxyphenyl radical or an α- or β-oxythienyl radical, which can in turn be mono-, di- or tri-substituted in the nucleus by halogen, trifluoromethyl and/or alkyl or alkoxy with in each case 1-6 C atoms.

The invention also relates to a process for the preparation of the prostacyclin derivatives of the formula I, which comprises (a) cyclizing a compound of the formula II

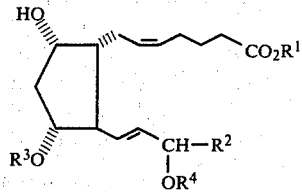

in which $R^1$ and $R^2$ have the meanings indicated for formula I and $R^3$ and $R^4$ can be identical or different and denote hydrogen or a protective group which can easily be split off, in the presence of a suitable electrophilic reagent to give a compound of the formula III

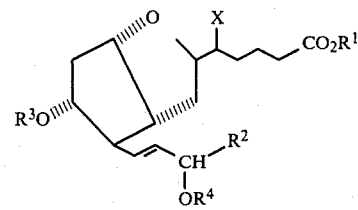

in which $R^1$ and $R^2$ have the meanings indicated for formula I, $R^3$ and $R^4$ have the meaning indicated for formula II and X denotes chlorine, bromine or iodine, ($a_1$) if $R^3$ and/or $R^4$ in a compound of the formila III denote a protective group, optionally splitting off this group whereupon a compound of the formula III in which $R^1$ and $R^2$ have the meanings indicated for formula I, X has the meanings indicated for formula III and $R^3$ and $R^4$ denote hydrogen is obtained, (b) splitting off HX from a compound of the formula III, whereupon a compound of the formula IV

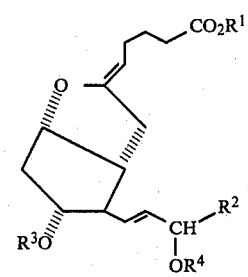

in which $R^1$ and $R^2$ have the meanings indicated for formula I and $R^3$ and $R^4$ have the meanings indicated for formula II is obtained, (c) if $R^3$ and/or $R^4$ in a compound of the formula IV do not denote hydrogen but a protective group, splitting off this group under suitable neutral or alkaline conditions, whereupon a compound of the formula I in which $R^1$ and $R^2$ have the meanings indicated for formula I is formed, ($c_1$) if appropriate, if $R^3$ and/or $R^4$ do not denote hydrogen but a protective group, splitting this off from a compound of the formula III simultaneously with HX, whereupon a compound of the formula I in which $R^1$ and $R^2$ have the meanings indicated for formula I is obtained, (d) if appropriate esterifying a compound of the formula I in which $R^1$ denotes hydrogen or a cation and $R^2$ has the meanings indicated for formula I, to give a compound of the formula I in which $R^1$ is an alkyl radical with the meaning indicated for formula I and $R^2$ has the meaning indicated for formula I, (e) if appropriate, saponifying a compound of the formula I in which $R^2$ has the meanings indicated for formula I and $R^1$ denotes an alkyl radical, to give a compound of the formula I in which $R^2$ has the meanings indicated for formula I and $R^1$ denotes hydrogen or a physiologically acceptable cation, and (f) if appropriate, in a compound of the formula I in which $R^2$ has the meaning indicated for formula I and $R^1$ denotes a physiologically acceptable metal ion or $NH_4$ ion, or ammonium ion which is derived from a primary, secondary or tertiary amine, replacing the cation $R^1$ by another cation.

Amongst the substituents mentioned, the following are preferred:

For $R^1$: hydrogen, a straight-chain or branched alkyl radical with up to six carbon atoms, a cycloaliphatic hydrocarbon radical with five to seven carbon atoms or a physiologically acceptable metal ion or $NH_4$ ion, or ammonium ion which is derived from a primary, secondary or tertiary amine.

For $R^2$: a cycloalkyl radical with 5–7 carbon atoms or a straight-chain or branched alkyl radical which has up to five carbon atoms and can be substituted by (a) fluorine, chlorine or an α- or β-thienyl radical or an α- or β-furyl radical, which can in turn be substituted by halogen, trifluoromethyl and/or alkyl or alkoxy with in each case 1–6 C atoms, or (b) an oxyphenyl radical or an α- or β-oxythienyl radical, which can in turn be mono-, di- or trisubstituted in the nucleus by halogen, trifluoromethyl and/or alkyl or alkoxy with in each case 1–6 C atoms.

Amongst the substituents for $R^2$, those listed below are very particularly preferred: 1-fluoropentyl, 1-chloropentyl, 5-fluoropentyl, 5-chloropentyl, 3-thienyl-2-ethyl, 2-thienyl-2-ethyl, 3-(2-chloro-thienyl)-2-ethyl, 2-(5-chloro-thienyl)-2-ethyl, phenoxymethyl, 3-chlorophenoxymethyl, 3-trifluoromethyl-phenoxymethyl, 3-thienyloxymethyl, 2-thienyloxymethyl, 3-(2-chloro-thienyl)-oxymethyl), 2-(5-chlorothienyl)oxymethyl, 3-furyl-2-ethyl, 2-furyl-2-ethyl, cyclopentyl, cyclohexyl and cycloheptyl.

The prostaglandin derivatives of the general formula II used as the starting material in the process according to the invention can be prepared by processes analogous to those such as are described, for example, in JACS 91, 5675 (1969), Tetrahedron Lett., 1970, 311, Netherlands Pat. No. 7,206,361 and Netherlands Pat. No. 7,209,758, and in German Offenlegungsschrift No. 2,524,955 and German Offenlegungsschrift No. 2,742,407.

Electrophilic reagents which react with γ-hydroxyolefins to form tetrahydrofuran derivatives by cyclization, such as, for example, iodine, iodine chloride, $KI_3$, N-bromoimides, such as N-bromosuccinimide and N-bromocamphorimide, or 1,3-dibromo-5,5-dimethylhydantoin, are suitable for the cyclization of compounds of the formula II to give compounds of the formula III. The reaction is preferably carried in an inert solvent, such as, for example, water, methylene chloride, chloroform diethyl ether, tetrahydrofuran or 1,2-dimethoxyethane. Heterogeneous or homogeneous solvent mixtures can also be used. The reaction can be carried out at temperatures between $-70°$ and $+30°$ C., if appropriate in the presence of an acid-binding agent, such as, for example, calcium carbonate, sodium carbonate or sodium bicarbonate. A preferred embodiment of the process consists in stirring a compound of the general formula II with 1.2–3 equivalents of $KI_3$ in water at $0°–10°$ in the presence of sodium carbonate and under an inert gas, reducing the excess $KI_3$ with sodium thiosulfate solution and extracting the cyclization product III (X=I) with chloroform. The product can be further reacted without special purification.

If $R^3$ and/or $R^4$ in a compound of the formula III denote a protective group, this can optionally be split off. This is appropriate if it is a protective group which must be removed with acid catalyst, such as, for example, an acetal group or tetrahydropyranyl group, since compounds of the formula IV are unstable to acid. The protective groups can appropriately be split off with acid catalysis in an alcoholic or aqueous/organic solvent. Suitable acids are dilute mineral acids or organic acids, such as p-toluenesulfonic acid, oxalic acid or acetic acid. If the protective group is an acyl group, this can be split off in an alkaline medium.

The splitting off of HX from compounds of the formula III with the formation of compounds of the general formula IV proceeds under the influence of bases in the presence or absence of a solvent.

Possible bases are both inorganic and organic bases such as, for example, alkali metal hydroxides or carbonates, alcoholates such as, for example sodium methylate or potassium tertiary butylate, amines such as, for example, triethylamine, 4-dimethylaminopyridine, dicyclohexylethylamine or 1,4-diazabicyclo[2,2,2]octane, or amidines such as, for example, 1,5-diazabicyclo[3,4,0]-non-5-ene (DBN) or 1,5-diazabicyclo[5,4,0]undec-5-ene (DBU).

If $R^3$ and/or $R^4$ in a compound of the formula IV do not denote hydrogen but a protective group, such as, for example, an acyl group, this group can be split off under mild alkaline conditions, for example with sodium carbonate or potassium carbonate in alcoholic or alcoholic-aqueous solution. This reaction is carried out at $-10°$ to $+30°$ C.

HX and the protective groups $R^3$ and/or $R^4$, if they denote acyl groups, can also be split off simultaneously from compounds of the formula III. A suitable reaction is, for example, that with alkali metal hydroxides or metal alcoholates in water or a lower alkyl alcohol, such as, for example, sodium methylate in methanol. The prostacyclin derivative of the formula I can thereby be obtained directly.

Compounds of the formula I in which $R^1$ denotes hydrogen or a cation and $R^2$ has the meanings indicated for formula I can be esterified to give compounds of the formula I in which $R^1$ denotes an alkyl radical. Because of the instability of the enol ether structure in the prostacyclin molecule, only processes which proceed rapidly and under mild conditions in a neutral or weakly acid medium, or advantageously in an alkaline medium, can be used for this esterification. Thus, for example, a prostacyclin derivative of the formula I ($R^1$=H) can be esterified with diazoalkanes of the formula $R^1$–$N_2$ ($R^1$=alkyl) at temperatures between $-40°$ and $+20°$, it being possible to use the customary solvents, such as, for example, diethyl ether, tetrahydrofuran, chloroform or low-molecular alcohols, such as methanol. The resulting esters can be isolated in a simple manner by evaporating off the solvent and, if appropriate, they can be purified by chromatography. A preferred esterification method consists in reacting the salt of the corresponding prostacyclin derivative I ($R^1$=a cation) with an alkylating agent $R^1$—X in the presence of a base such as, for example, a metal alcoholate or metal carbonate, in a suitable solvent. Possible metal alcoholates are, for example, sodium methylate, sodium ethylate or potassium tertiary butylate, and suitable carbonates are, for example, calcium carbonate or sodium bicarbonate. Suitable solvents which are possible are alcohols such as, for example, methanol or tert.-butanol, ethers such as tetrahydrofuran or 1,2-dimethoxyethane, and, in particular, dipolar aprotic solvents such as dimethylformamide, dimethylsulfoxide, acetonitrile or N-methylpyrrolidone. In the alkylating agents $R^1$—X, X preferably denotes bromine, iodine or a sulfonic acid radical.

Compounds of the formula I in which $R^1$ denotes an alkyl radical can be saponified in the customary manner in an alkaline medium to give compounds of the formula I in which $R^1$ denotes hydrogen or, preferably, a cation, for example using NaOH or KOH in a low-molecular alcohol such as methanol, or an ether such as dimethoxyethane or tetrahydrofuran, if appropriate in the presence of water. An equimolar amount or a very slight excess of an alkali metal hydroxide is advantageously used so that the alkali metal salt of the formula I ($R^1$=an alkali metal ion) is obtained by evaporating off the solvent.

The alkali metal cation can be replaced by any other cations on ion exchangers in the customary manner. For this, a solution of the alkali metal salt of a claimed prostacyclin derivative is allowed to run through a column packed with a cation exchanger such as, for example, Amberlite CG-50 or Dowex CCR-2.

The cation exchanger is charged with the desired cation, for example with an ammonium ion which is derived from a primary, secondary or tertiary amine. The desired salt is obtained by evaporating the eluate.

The compounds of the general formulae II and III can be employed for the subsequent reactions as a mixture of diastereomers, with regard to the position of the hydroxyl groups on carbon atom 15 (prostaglandin nomenclature), as pure α- or β-isomers or in the form of optically active antipodes. However, the stereoisomers or antipodes can also be separated after any subsequent reaction stage. This means that all the reactions described can be carried out with mixture of diastereomers, pure diastereomers or optically active antipodes.

If the individual reaction products are not already obtained in a form which is sufficiently pure that they can be employed for the following reaction step, purification by means of, for example, column chromatography, thin layer chromatography or high-pressure liquid chromatography is advisable.

In addition to the compounds mentioned in the examples, the following compounds, in particular, can also be prepared by the process according to the invention: 20-fluoro-$PGI_2$ methyl ester, 16-chloro-$PGI_2$, 16-chloro-$PGI_2$ methyl ester, 17-(2-thienyl)-18,19,20-trinor-$PGI_2$ methyl ester, 17-(3-(2-chlorothienyl))-18,19,20-trinor $PGI_2$, 16-phenoxy-17,18,19,20-tetranor-$PGI_2$ ethyl ester, 16-(3-trifluoromethyl-phenoxy)-17,18,19,20-tetranor-$PGI_2$-n-butyl ester, 16-(3-(2-chloro)thienyloxy)-17,18,19,20-tetranor-$PGI_2$ methyl ester, 16-(2-thienyloxy)-17,18,19,20-tetranor-$PGI_2$, 17-(3-furyl)-18,19,20-trinor-$PGI_2$, 15-cyclopentyl-16,17,18,19,20-pentanor-$PGI_2$ propyl ester and 15-cyclopentyl-16,17,18,19,20-pentanor-$PGI_2$.

The compounds according to the invention are distinguished by: (1) an inhibitory action on thrombocyte aggregation; (2) relaxation of the vascular walls, in particular of the coronary arteries; and (3) hypotensive properties. They can thus be used as medicaments.

A possible unit dose for hypotensive action is 0.1 μg/kg–10 μg/kg, preferably 5 μg/kg–100 μg/kg, of body weight, and a possible daily dose is 0.001 mg/kg–1 mg/kg, preferably 0.05 mg/kg–1 mg/kg, of body weight.

The same doses or even smaller doses can be used for the two other indications.

Pharmacological parameters of the compounds of the general formula I ($R^1 = CH_3$)

| Example | $R^2$ = | Lowering of blood pressure, μg/kg, intravenous administration (rats) | | | | Relaxation of coronary arteries in cattle in % relative to the particular standard | | | | Blood platelet aggregation |
|---|---|---|---|---|---|---|---|---|---|---|
| | | ED 25 | Dose | % | Period of action minutes | 1 | 10 | 100 | 1,000 ng/ml | |
| 2d | –⟨H⟩ | 0.23 | 0.1 | −7 | 2.4 | 14 | 40 | 89 | | $5 \times 10^{-7}$ |
| | | | 0.3 | −28 | 7.4 | | | | | |
| | | | 1.0 | −61 | 18.0 | | | | | |
| 2a | $CH_2$–O–⟨S⟩ | 0.23 | 0.1 | −13 | 2.4 | 34 | 74 | 152 | | |
| | | | 0.3 | −19 | 4.2 | | | | | |
| | | | 1.0 | −46 | 6.4 | | | | | |
| 2c | –$CH_2$O–⟨Cl⟩ | Slight lowering (15 mm Hg) on intravenous administration of 1 μg/kg | | | | 250 / 41 | 500 / 106 | 1000 / 257 | | $4 \times 10^{-6}$ |
| 2f | –$CH_2$–$CH_2$–⟨O⟩ | 0.31 | 0.1 | −6 | 1.7 | 14 | 31 | 60 | | $4 \times 10^{-7}$ |
| | | | 0.3 | −20 | 4.4 | | | | | |
| | | | 1.0 | −49 | 11.0 | | | | | |
| 2e | F-alkyl | 0.93 | 0.1 | −3 | 0.4 | 24 | 48 | 105 | | $9 \times 10^{-8}$ |
| | | | 1.0 | −24 | 4.1 | | | | | |
| | | | 10.0 | −52 | 8.0 | | | | | |
| | | | 100.0 | −64 | 28.8 | | | | | |

| | | Pharmacological parameters of the compounds of the general formula I ($R^1$ = Na) | | | | | | | |
|---|---|---|---|---|---|---|---|---|---|
| | | Lowering of blood pressure, μg/kg, intravenous administration (rats) | | | | Relaxation of coronary arteries in cattle in % relative to the particular standard | | | Blood platelet aggregation |
| Example | $R^2$ = | ED 25 | Dose | % | Period of action minutes | 1 | 10 | 100 | 1,000 ng/ml | |
| 3a |  | 0.25 | 0.1 | −12 | 1.0 | 29 | 50 | 115 | | $5 \times 10^{-9}$ |
| | | | 1.0 | −46 | 4.2 | | | | | |
| | | | 10.0 | −58 | 15.1 | | | | | |
| 3d | | 0.39 | 0.1 | −5 | 0.7 | 13 | 25 | 79 | | |
| |  | | 0.3 | −17 | 1.8 | | | | | |
| | | | 1.0 | −42 | 4.5 | | | | | |
| 3d |  | 0.27 | 0.1 | −11 | 2.0 | 14 | 32 | 75 | | $2 \times 10^{-8}$ |
| | | | 1.0 | −46 | 5.2 | | | | | |
| | | | 10.0 | −64 | 16.6 | | | | | |
| | | | 100.0 | −68 | 33.0 | | | | | |

The compounds of formula I according to the invention can be used as the free acid, but preferably in the form of their physiologically acceptable inorganic or organic salts or as esters.

The acids and salts or esters can be used in the form of their aqueous solutions or suspensions, or also as solutions or suspensions in pharmacologically acceptable organic solvents, such as monohydric or polyhydric alcohols, for example ethanol, ethylene glycol or glycerol; oils such as, for example, sunflower oil or cod-liver oil; ethers such as, for example, diethylene glycol dimethyl ether; or also polyethers such as, for example polyethylene glycol; or also in the presence of other pharmacologically acceptable polymeric excipients such as, for example, polyvinylpyrrolidone.

Possible formulations are the customary galenical infusion or injection solutions and tablets, as well as formulations which can be applied locally, such as creams emulsions, suppositories or aerosols.

A further way of using the new compounds is in combination with other active compounds. These include, in addition to other suitable substances, above all: circulatory agents in the broadest sense, for example cardiac glycosides such as digitoxin; sympathomimetic agents such as Suprifen; β-sympatholytic agents such as Inderal; coronary dilators such as Chromonar or prenylamine; hypotensive substances such as reserpine or clonidine; antiarrythmic agents; substances which stimulate the blood flow; anticoagulants or fibrinolytic agents; diuretic agents, such as, for example, furosemide; substances which lower the lipid level or substances for use in geriatrics and other preparations which have an effect on metabolism; prostaglandins or prostaglandin antagonists or prostaglandin biosynthesis inhibitors such as, for example, non-steroid antiphlogistic agents; thromboxane synthetase inhibitors; psychopharmaceuticals; and vitamins.

The compounds of the formula III and IV are new, valuable intermediate products for the preparation of compounds of the formula I.

EXAMPLE 1

(a) 5-Bromo-16-(3-thienyloxy)-17,18,19,20-tetranor-PGI$_1$ (III)

132 mg of N-bromosuccinimide are added to 360 mg of 16-(3-thienyloxy)-18,19,20-tetranor-PGF$_{2\alpha}$11,15-bis-tetrahydropyranyl ether in 7 ml of tetrahydrofuran/chloroform, 1:1, while stirring and under argon. After 2 hours, chloroform and aqueous sodium thiosulfate solution are added and the organic layer is evaporated, after drying with magnesium sulfate. The residue is warmed in 5 ml of glacial acetic acid/water/tetrahydrofuran, 3:1:1, to 45° for five hours, under argon, and the solvent is then evaporated off in vacuo. The residue can be purified by column chromatography on about 20 g of silica gel. Ethyl acetate/glacial acetic acid, 99:1, is used as the eluting agent. NMR: as for Example (1c).

(b) 5-Iodo-16-(3-thienyloxy)-17,18,19,20-tetranor-PGI$_1$ methyl ester (III)

200 mg of 16-(3-thienyloxy)-17,18,19,20-tetranor-PGF$_{2\alpha}$ methyl ester (II) are dissolved in 1.5 ml of diethyl ether and, after adding 0.3 g of potassium bicarbonate in 1 ml of H$_2$O, the mixture is cooled to 0°, under argon. 5.4 ml of a 2.5% strength solution of iodine in ether are added dropwise in the course of 2 hours, and thereafter the mixture is stirred for a further two hours at 0°. After adding about 10 ml of ether, the organic layer is washed first with sodium thiosulfate solution and then with water, dried and evaporated. The reaction product is sufficiently pure, but can be freed from small amounts of impurities by chromatography on silica gel (cyclohexane/ethyl acetate, 2:8).

Yield: 250 mg, R$_f$ value in ethyl acetate=0.54, NMR: as for Example (1c).

(c) 5-Iodo-16-(3-thienyloxy)-17,18,19,20-tetranor-PGI$_2$ methyl ester (III)

200 mg of 16-(3-thienyloxy)-17,18,19,20-tetranor-PGF$_{2\alpha}$ methyl ester (II) are stirred together with 50.8 mg of iodine, 66 mg of potassium iodide and 42.4 mg of sodium carbonate in 2 ml of water at 5°–10° C. for two hours, under an inert gas. The excess iodine is then decolorized with sodium thiosulfate solution and the reaction mixture is extracted with chloroform. The organic phase is washed with water, dried and evaporated.

Yield: 244 mg; R$_f$ value in ethyl acetate=0.54

NMR: δ=5.5–5.7 (m, 2H) olefinic protons, 3.60 (S,3H) O—CH$_3$, 1.1–2.7 (m,12H) —CH$_2$— and >CH—, and 6.15–7.7 (m,3H) thiophene.

(d) 5-Iodo-17-(3-thienyl)-18,19,20-trinor-PGI$_1$ methyl ester (III)

Obtained from 17-(3-thienyl)-18,19,20-trinor-PGF$_{2\alpha}$ methyl ester (II) by a reaction analogous to Example (1c).

NMR: δ=1.1–2.9 (m,16H), CH$_2$ and —CH—, 3.6 (S,3H) OCH$_3$, 5.5–5.65 (m,2H) olefinic protons, and 6.9–7.3 (m,3H) thiophene.
R$_f$=0.48 (ethyl acetate/acetic acid=97.5/2.5).

(e) 5-Iodo-16-(3-chlorophenoxy)-17,18,19,20-tetranor-PGI$_1$ methyl ester (III)

Obtained from 16-(3-chlorophenoxy)-17,18,19,20-tetranor-PGF$_{2\alpha}$ methyl ester (II) by a reaction analogous to Example (1c).
NMR: δ=1.2–2.8 (m,12H) CH$_2$ and —CH—, 3.7 (S,3H) OCH$_3$, 4.0 (d,2H) —CH$_2$—O—, 4.15 (1H) —CH—I—, 4.3–4.8 (m,3H) —CH—OH, 5.7–5.9 (m,2H) olefinic protons, and 6.7–7.4 (m,4H) aromatic protons.
R$_f$ value (ethyl acetate)=0.35

(f) 5-Iodo-15-cyclohexyl-16,17,18,19,20-pentanor-PGI$_1$ methyl ester (III)

Obtained from 15-(cyclohexyl)-16,17,18,19,20-pentanor-PGF$_{2\alpha}$ methyl ester (II) by a reaction analogous to Example (1b).
NMR: δ=0.8–2.8 (m,23H) —CH$_2$ and —CH—, 3.6 (S,3H) OCH$_3$ and 5.5–5.6 (m,2H) olefinic protons.

(g) 5-Iodo-16-fluoro-PGI$_1$ methyl ester (III)

Obtained from 16-fluoro-PGF$_{2\alpha}$ methyl ester (II) by a reaction analogous to Example (1b).
NMR: δ=0.9–2.9 (m,21H) —CH$_2$— and —CH—, 3.65 (S,3H) OCH$_3$ and 5.6–5.7 (m,2H) olefinic protons.

(h) 5-Iodo-17-(2-furyl)-18,19,20-trinor-PGI$_1$ methyl ester (III)

Obtained from 17-(3-furyl)-18,19,20-trinor-PGF$_{2\alpha}$ methyl ester (II) by a reaction analogous to Example (1c).
NMR: δ=1.0–2.9 (m,12H) —CH$_2$— and —CH—, 3.6 (S,3H) —OCH$_3$, 5.5–5.6 (m,2H) olefinic protons, 5.9–6.05 and 6.15–6.3 (m,2H) aromatic protons and 7.2–7.35 (m,1H) aromatic protons.

(i) 5-Iodo-17-(3-thienyl)-18,19,20-trinor-PGI$_1$ methyl ester 11,15-bistetrahydropyranyl ether (III, R$^3$ and R$^4$=tetrahydropyranyl)

Obtained from 17-(3-thienyl)-18,19,20-trinor-PGF$_{2\alpha}$ methyl ester 11,15-bistetrahydropyranyl ether (II, R$^3$ and R$^4$=tetrahydropyranyl) by a reaction analogous to Example (1c).
Colorless oil, R$_f$ value in ethyl acetate: 0.89

EXAMPLE 2

(a) 16-(3-Thienyloxy)-17,18,19,20-tetranor-PGI$_2$ methyl ester (I)

300 mg of 16-(thienyloxy)-5-bromo-17,18,19,20-tetranor-PGI$_1$ (Example 1a) are warmed with 224 mg of potassium tertiary butylate in 10 ml of tert.-butanol to 45°–50° under an argon atmosphere. After stirring the mixture for two hours, the solvent is evaporated off in vacuo, ice-water and cold ether are added to the residue and the aqueous phase is brought rapidly to pH 5 with a cold solution of sodium dihydrogen phosphate. Excess diazomethane in cold ether is immediately added to the ether phase. After stirring the mixture at −5° to 0° for the 30 minutes, the product is purified on 15 g of silica gel, which had previously been suspended in a mixture of ethyl acetate/triethylamine, 95:5, for some hours. Ethyl acetate/triethylamine, 98:2, is used as the eluting agent.
R$_f$=0.15 (15α-epimer) (in ethyl acetate/0.5% strength N(C$_2$H$_5$)$_3$)
NMR: δ=1.1–2.8 (m,12H) CH$_2$ and CH, 2.8–3.0 (S,2H) OH, 3.6 (m,3H) OCH$_3$, 5.6–5.7 (m,2H) olefinic protons, and 6.2–7.2 (m,3H) thiophene.

(b) 17-(3-Thienyl)-18,19,20-trinor-PGI$_2$ methyl ester (I)

290 mg of 5-iodo-17-(3-thienyl)-18,19,20-trinor-PGI$_1$ methyl ester (Example 1d) are stirred with 1.3 ml of 1,5-diazobicyclo[5,4,0]undec-5-ene at room temperature. After 130 minutes, the reaction has ended. 3 ml of ice-water are added to the reaction solution and the product is extracted three times with ether. The organic phase is dried with anhydrous sodium sulfate and evaporated and the residue is purified, as described above in Example 2a, on silica gel with ethyl acetate/triethylamine, 98:2.
R$_f$ value=0.17 (15α-epimer) (in ethyl acetate/0.5% strength N(C$_2$H$_5$)$_3$)

(c) 16-(3-Chlorophenoxy)-17,18,19,20-tetranor-PGI$_2$ methyl ester (I)

Obtained from 5-iodo-16-(3-chlorophenoxy)-17,18,19,20-tetranor-PGI$_1$ methyl ester (Example 1e) by a reaction analogous to Example (2b).
NMR: δ=3.6 (S,3H) OCH$_3$, 4.0 (d,2H) —CH$_2$O—, 5.7–5.9 (m,2H) olefinic protons, and 6.7–7.3 (m,4H) aromatic protons.
R$_f$ value=0.22, running agent: ethyl acetate/Et$_3$N, 50/1; SiO$_2$ plates pre-treated with ether/Et$_3$N (3:1)

(d) 15-Cyclohexyl-16,17,18,19,20-pentanor-PGI$_2$ methyl ester (I)

Obtained from 5-Iodo-15-cyclohexyl-16,17,18,19,20-pentanor-PGI$_1$ methyl ester (Example 1f) by a reaction analogous to Example (2).
NMR: δ=0.8–2.8 (m,23H) —CH$_2$— and —CH—, 3.65 (S,3H) OCH$_3$, 3.65–4.8 (m,4H) —CHOH and —O—C=CH and 5.5–5.7 (m,2H) olefinic protons.

(e) 16-Fluoro-PGI$_2$ methyl ester (I)

Obtained from 5-iodo-16-fluoro-PGI$_1$ methyl ester (Example 1g) by a reaction analogous to Example (2b).
NMR: δ=0.9–2.8 (m,22H) —CH$_2$— and —CH—, 3.6 (S,3H) OCH$_3$, 3.6–4.8 (m,4H) —CH—OH and —O—C=CH— and 5.5–5.7 (m,2H) olefinic protons.

(f) 17-(2-Furyl)-18,19,20-trinor-PGI$_2$ methyl ester (I)

Obtained from 5-iodo-17-(3-furyl)-18,19,20-trinor-PGI$_1$ methyl ester (Example 1h) by a reaction analogous to Example (2b).
NMR: δ=1.0–2.85 (m,12H) —CH$_2$— and —CH—, 3.6 (S,3H) OCH$_3$, 3.6–4.8 (m,4H) —CHOH and —O—C=CH—, 5.9–6.05 and 6.15–6.3 (m,2H) aromatic protons and 7.2–7.35 (m,1H) aromatic protons.

(i) 17-(3-Thienyl)-18,19,20-trinor-PGI$_2$ methyl ester 11,15-bistetrahydropyranyl ether (IV, R$^3$ and R$^4$=tetrahydropyranyl Obtained from 5-iodo-17-(3-thienyl)-18,19,20-trinor-PGI$_1$ methyl ester 11,15-bistetrahydropyranyl ether (Example 1i) by a reaction analogous to Example (2b).
Colorless oil; R$_f$ value=0.85 in ethyl acetate.

EXAMPLE 3

(a) The sodium salt of
16-(3-thienyloxy)-17,18,19,20-tetranor-PGI$_2$ (I)

268 mg (0.5 mmole) of 5-iodo-16-(3-thienyloxy)-17,18,19,20-tetranor-PGI$_1$ methyl ester Example (1c) are dissolved in 50 ml of a 90% strength ethanol. A solution of 57.5 mg of sodium in 5 ml of ethanol are added to this solution, while stirring. The mixture is stirred at 60° C. under argon for 3 hours, the solution is filtered over active charcoal and the solvent is removed from the filtrate in vacuo at −10° C. (freeze-drying). The sodium salt of the prostaglandin derivative is obtained as a colorless powder.

(b) The potassium salt of
16-(3-thienyloxy)-17,18,19,20-tetranor-PGI$_2$ (I)

192 mg of pure 16-(3-thienyloxy)-17,18,19,20-tetranor-PGI$_1$ methyl ester (Example 2a), 1.1 ml of 0.5 M potassium hydroxide solution and 2 ml of methanol are left to stand under an inert gas at room temperature for 24 hours. The methanol is stripped off in vacuo and the aqueous solution of the potassium salt is freeze-dried. The potassium salt of the prostacyclin derivative is obtained as a colorless powder.

(c) The triethylammonium salt of
16-(3-thienyloxy)-17,18,19,20-tetranor-PGI$_2$

An aqueous solution of 50 mg of the sodium salt of 16-(3-thienyloxy)-17,18,19,20-tetranor-PGI$_2$ (Example 3b) is discharged onto a column containing 15 g of Amberlite CG-50 (triethylammonium form). The column is eluted with a 3% strength aqueous solution of triethylammonium carbonate. The product is obtained as a crystalline powder (decomposition >50° C.) by freeze-drying the eluate.

(d) The corresponding alkali metal salts or ammonium salts can be prepared, analogously to Examples 3a to c, from the compounds of Examples 1a to 1f or 2a–2f by alkaline saponification of the ester or (compare Example 3a) by elimination of HX and simultaneous saponification of the ester and, if appropriate, chromatography on ion exchangers.

We claim:

1. A compound selected from the group consisting of 16-(3-thienyloxy)-17,18,19,20-tetranor-prostacyclin methyl ester and 17-(2-furyl)-18,19,20-trinor-prostacyclin methyl ester.

2. A compound as in claim 1 which is 16-(3-thienyloxy)-17,18,19,20-tetranor-prostacyclin methyl ester.

3. A compound as in claim 1 which is 17-(2-furyl)-18,19,20-trinor-prostacyclin methyl ester.

4. A pharmaceutical composition for the treatment of hypertension, which composition comprises a therapeutically effective amount of a compound as in claim 1 and a pharmaceutical carrier therefor.

5. A method for treating high blood pressure in a patient requiring such treatment, which method comprises orally, parenterally, or locally administering to said patient a therapeutically effective amount of a compound as in claim 1.

* * * * *